United States Patent [19]
Posca

[11] Patent Number: 4,802,846
[45] Date of Patent: Feb. 7, 1989

[54] AUTOMATIC SURVEYOR FOR DENTAL MODELS

[76] Inventor: Jorge E. Posca, Star Road #1, Box 440, Rosemond, Calif. 93560

[21] Appl. No.: 42,720

[22] Filed: Apr. 27, 1987

[51] Int. Cl.⁴ .............................................. A61C 3/00
[52] U.S. Cl. ........................................ 433/75; 433/32
[58] Field of Search ............................ 433/32, 76, 75

[56] References Cited
U.S. PATENT DOCUMENTS 3,522,654 8/1970 Schoelz .................................. 433/32
4,493,644 1/1985 Ai et al. ................................. 433/75

Primary Examiner—Robert Peshock
Attorney, Agent, or Firm—James T. English

[57] ABSTRACT

Apparatus and method for applying dental wax, simulating natural gingiva, to denture models uses controlled temperature and pressure to maintain the wax at constant viscosity and flow rate. Placement of the flow nozzle to fill recesses in the model where the simulated gum tissue should be, can be manual or microprocessor program controlled in combination with a micropositioner.

5 Claims, 2 Drawing Sheets

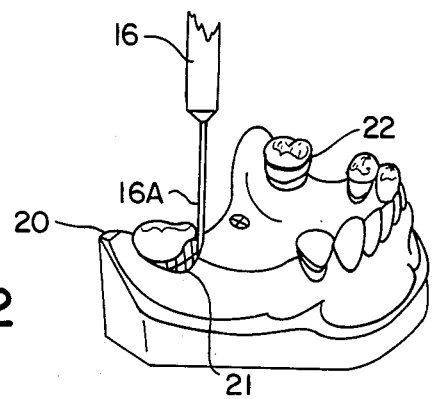
FIG. 2
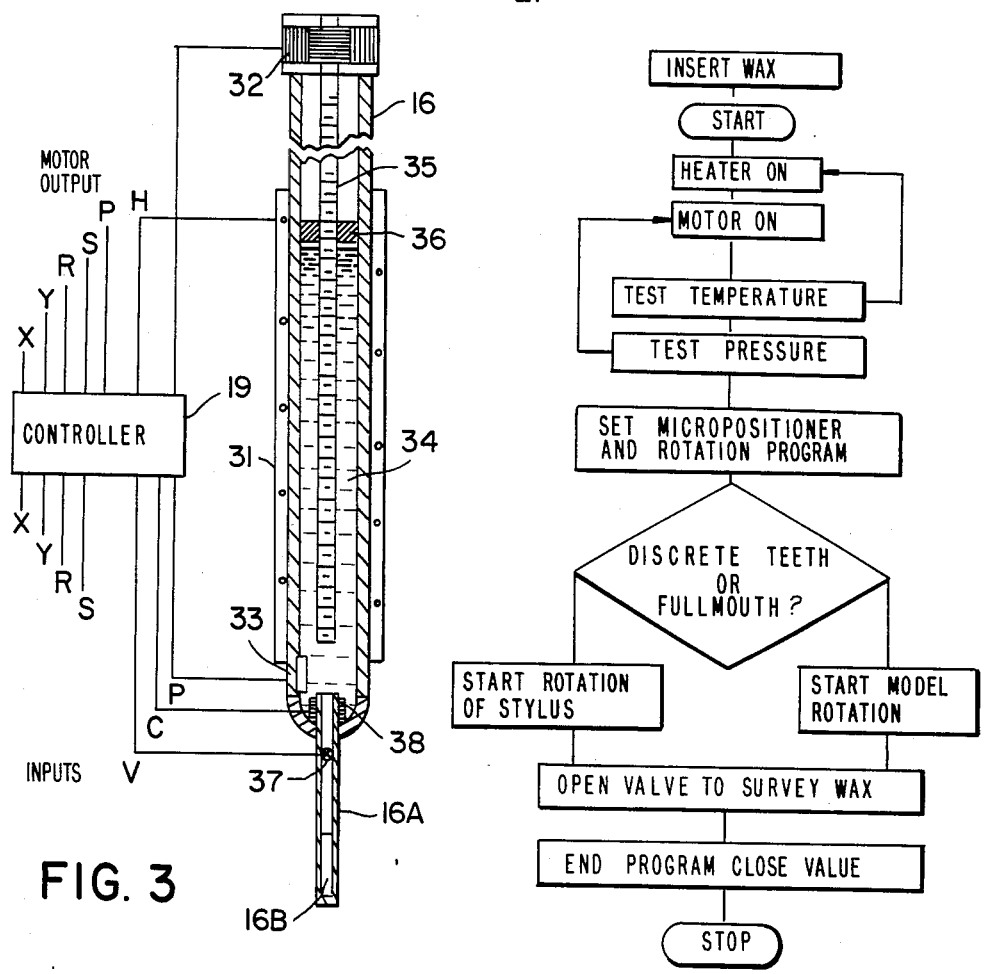
FIG. 3
FIG. 4

AUTOMATIC SURVEYOR FOR DENTAL MODELS

BACKGROUND OF THE INVENTION

The invention relates to methods and apparatus for the production of dentures and more specifically to automated or semiautomated procedures for surveying the dental wax used in simulating the natural gingiva or gum tissue between the artificial teeth and the simulated buccal tissue on the model. In modern dental laboratories the surveying of the dental wax is still a very time consuming manual art which leads to nonuniformity in the strength and texture of the wax coating on the denture, and possible fracture in use. Prior art used a procedure of melting discrete pieces of wax on a Bunsen burner and manually placing the melt in position on the model with a stylus. Hot wax guns have also been used.

SUMMARY OF THE INVENTION

In accordance with the invention, a cylinder including a heater to melt the wax and a pressure sensor to monitor the pressure and hence the viscosity of the melt is vertically mounted over a micromanipulator which positions the efflux of the pump onto a model containing the denture. The model contains the artificial teeth mounted in accordance with an impression taken of the mouth, and includes recessed areas around the teeth and in the area of the gums. Surveying the wax into these areas is done in one embodiment of the invention by automatically flowing the melted wax onto the model in the proper area as controlled by a micropositioner capable of rotation and translation, in accordance with a program controlled by a controller. The proper flow of wax is dependent upon maintaining the wax at a constant viscosity and pressure. This is done by the pump which maintains the temperature of the wax and thus the viscosity thereof, and by the motor which drives the pump piston so that the pressure of melt at the orifice of the pump is constant. Feedback through the controller maintain the temperature and pressure at constant values. The model is mounted with teeth facing upward, on a turntable mounted on an x - y positioner, so that each tooth location is accessible to a fixed-position stylus that surveys the wax through a side slot. As the model is rotated, in the case of continuous; i.e., no-gap models of a denture or partial, the turntable rotates, and the micropositioner moves to place the equator of each tooth against the stylus, in turn. The wax is dispensed while the model is moving. If there are gaps between the teeth, of sufficient width for the stylus to fit between two teeth, the stylus is rotated, with accompanying x - y coordinate change, to survey wax around the tooth. The stylus is maintained in a vertical orientation at all times, for surveying the wax between the equator of the tooth and the simulated buccal tissue at the base of the tooth.

The entire process of surveying the wax can be done under program control wherein a microprocessor is programmed to move the x - y coordinates of the model in relation to the position of the stylus as determined by a six quadrant contact sensor at the base of the stylus in the pump probe. The stylus and its associated pump can be slipped out of its mounting and used manually when desired.

BRIEF DESCRIPTION OF THE DRAWINGS

FIG. 2 is a view of a model in the vertical position for surveying wax into the recesses thereof.

FIG. 3 is a sectional view of the pump and its components that interface with the controller.

FIG. 4 is a flow diagram of the automatic operation of the invention, controlled by the controller

DESCRIPTION OF THE PREFERRED EMBODIMENTS

Figure 1:
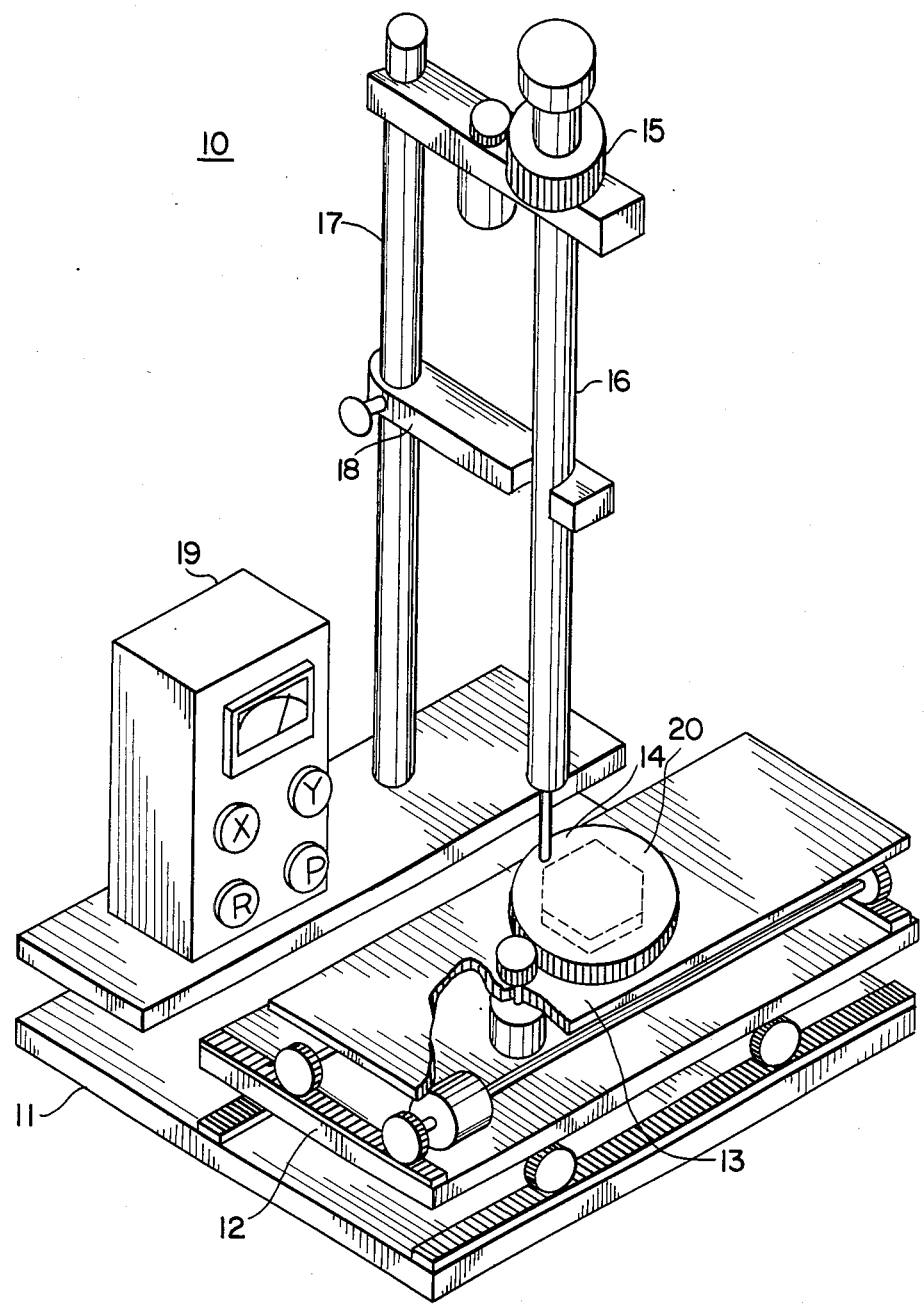
FIG. 1 is an isometric view of the essential elements of the invention including the x - y micropositioner, the turntable, the pump and stylus, and the controller.

FIG. 1 shows the base 11 of the automatic surveyor which holds the x-axis mechanism of the micropositioner of well known construction with electric motor drive and rack-and-pinion gearing. The base 12 and tracked gearing is the y-axis of the micropositioner, which moves the plate 13 and turntable 14 so that any tooth on the model 20 is accessible to the stylus by X,Y and R coordinates, either manually by control knobs of the controller 19, or by program control. The turntable 14 which rotates the model for surveying positions each tooth in turn against the probe and stylus 16 which can be rotated by gear 15 and its associated motor. The gear 15 is of a thickness that the probe 16 which is slidably mounted in the bracket and arm 17 so that the probe can move vertically in accordance with the contour of the simulated buccal tissue at the base of the tooth to be surveyed. The bracketarm 18 provides y-axis rigidity for the probe so that contact of the stylus with the tooth can be detected. When contact with the stylus 16A is detected, movement of the micropositioner is halted. Subsequently the automatic program is started and the coordinates for specific teeth are fed into the micropositioner; the turntable 14 begins to rotate; the probe 16 is rotated as required; and the wax, under constant temperature and pressure, is surveyed. When a tooth is surveyed through 360 degrees, the valve in the stylus is closed, and opened after rotation of the turntable and contact with the adjacent tooth is made.

Referring now to FIG. 2, we see an isometric view of a typical model in the existing art consistiong of a mounting and mold containing teeth to be surveyed. The crosshatched area 21 is typically an area where survey of wax is required. The area 21 extends from the equator 22 which is points on the vertical tangent around the tooth, to the simulated buccal tissue of the jaw. The probe 16 is oriented the vertical tangent and the stylus 16A has a vertical slot from which the wax issues. The slot must be oriented toward the tooth when surveying the wax.

Referring to FIG. 3, we see the probe 16 and stylus 16A. The probe constitutes a pressure vessel maintaining pressured wax melt. This figure illustrates the apparatus and the means for control of: the wax viscosity, the velocity of efflux of the wax through the stylus, and the timing of the efflux in relation to the position of any point on the model.

Both x - y coordinate and rotation motors R (turntable) and S (stylus) are controlled by controller 19, as is the maintenance of temperature H by heater 31 having a thermostat, and pressure by operating motor 32 in response to pressure sensor 33 to increase the pressure on the molten wax 34 by screw 35 and piston 36. Controller 19 also controls the opening and closing of the valve 37 in the stylus 16A in response the stylus contact sensor 38 output. The contract sensor 38 is a direction-sensing six-sectored contact switch which operates when the stylus has a very small pressure exerted on it in any direction.

The directional information is sent to the controller to rotate the stylus aperture 16B to the proper direction for survey and to stop the x - y coordinate motors until the pressure is released by the changing contour of the equator of the tooth. The coordinates are then changed to increase the pressure on the stylus.

The controller 19 contains programmed switching elements to perform the processing shown in the functional flow diagram of FIG. 4. The processing is as follows.

The motor 32 is removed from the cylinder 16, together with the drive screw 35 and piston 36. The solid wax material 34 is inserted, into the cylinder 16, and the motor assembly consisting of the motor 32, drive screw 35 and piston 36, are replaced in the cylinder 16. The heater 35 is then energized to melt the wax. After a period of time to melt the wax has elapsed, the motor 32 is energized to increase the pressure in the cylinder to a specific value as measured by the pressure transducer 33. The pressure specified is related to the viscosity of the wax melt and is critical to the desired flow characteristics through the output value 37 and onto the model 20. The micropositioner translation and rotation motors are then energized by the controller 19 and the orientation of the model is either automatically or manually advanced while the wax flow fills the recesses in the model.

In the automatic mode, for a full-mouth denture or a partial section, having essentially no space between the teeth a turntable rotation program is invoked; for a discrete tooth denture, a probe rotation program is included. After the denture model is completely surveyed, the valve 37 is closed and the process is stopped.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. Apparatus for dispensing hot wax in a pattern, which comprises:
   pressure vessel means for maintaining temperature and pressure of melted wax therein, having an outlet valve for dispensing the melted wax and an input for inserting raw wax material,
   means for positioning an article in relation to the outlet valve of said pressure vessel means, in fluid communication with the melted wax effluent from said pressure vessel valve, for forming a melted wax pattern on the article;
   controller means for maintaining the temperature of said pressure vessel constant, for maintaining the pressure in said pressure vessel constant, for operating said outlet valve and for controlling said means for positioning an article,
   whereby to dispense hot wax at constant viscosity and pressure in a pattern determined by the positioning of the article relative to the dispensing pressure vessel.

2. The apparatus for dispensing hot wax in pattern as described in claim 1, wherein the pressure vessel comprises:
   a cylinder substantially tubular, vertically orientated, having a removable top end and a bore in the closed top end, and an orifice in the bottom end, and an axis, said tube being heat conductive;
   an electric motor mounted at the top end of said cylinder coaxial therewith, said motor having an armature shaft extending into said cylinder through the bore in the closed end, said motor adapted to operate bidirectionally;
   a screw connected to said shaft, said screw extending along the axis of said cylinder to a point near the bottom end thereof;
   a piston, in said cylinder, mounted on said screw, adapted to move reciprocally in said cylinder as said motor is operated bidirectionally;
   a heater coil mounted on said cylinder near the bottom end adapted to heat the contents of said cylinder through the tube
   a pressure transducer mounted in said cylinder near the bottom end, adapted to sense the cylinder internal pressure, said transducer having an electrical output;
   a thermometer junction in thermal contact with said cylinder adapted to measure the temperature of the contents of the cylinder;
   an electrically operated output valve in the port in the bottom end of said cylinder, adapted to permit efflux of the contents of said cylinder, during electrical signal application.
   a positioning mechanism having a carriage, in fluid communication with the efflux of said electricaly operated valve, said mechanism adapted to translate and rotate the position of an article attached to said carriage.

3. Apparatus for dispensing hot wax in a pattern as described in claim 1, wherein the controller is a microprocessor programmed to apply electrical energy to the heater, to the motor, to the valve, and to the positioning mechanism, in the proper sequence to perform the method.

4. The method described in claim 5 wherein the temperature is maintained between 120 and 130 degrees Fahrenheit for commonly used dental utility wax.

5. In a method for surveying simulated gingiva wax on a dental model consisting of a substantially disk shaped base, horizontally disposed, having a central rotational axis; a cast made from a dental impression die including teeth, mounted coaxially with the base; a prosthesis frame including perforate areas for mounting artificial teeth at specified coordinate positions on the prosthesis to be surveyed, placed on the cast; artificial teeth mounted in the perforate areas prepared to receive artificial gingiva wax, the frame having clasps for clamping the prosthesis to the cast simulated natural teeth; the improvement, which comprises the steps of:
   mounting the model at the base on a micropositioner for rotation about the rotational axis, and translation about tooth position coordinates for exposure of tooth surfaces to a pressure vessel having a wax dispensing outlet stylus slotted to flow wax radially outwadly;
   rotating the model and translating the coordinates of the tooth to be surveyed to a central position placing the tooth to be surveyed in contact with the pressure vessel stylus while simultaneously rotating the stylus to direct the flow of wax around the curvature of the tooth;

sensing the equatorial surface of the tooth to initiate flow of wax;

flowing melted wax at constant temperature and pressure from the pressure vessel stylus in response to contact with the equaltorial surface of the tooth;

translating and rotating the coordinates of the next tooth to be surveyed into contact with the stylus, and depositing wax; and repeating the positioning and wax flowing for each tooth coordinate;

stopping the flow of wax after survey is completed by moving the model out of contact with the stylus;

whereby the method steps can be performed automatically under the direction of a programmed controller.

* * * * *